(12) United States Patent
Port

(10) Patent No.: US 7,341,711 B2
(45) Date of Patent: Mar. 11, 2008

(54) PORPHYRIN COMPOUNDS AND THEIR USE IN HIGH-FIELD MRI

(75) Inventor: Marc Port, Deuil la Barre (FR)

(73) Assignee: Guerbet, Villepinte (FR)

(*) Notice: Subject to any disclaimer, the term of this patent is extended or adjusted under 35 U.S.C. 154(b) by 205 days.

(21) Appl. No.: 11/077,033

(22) Filed: Mar. 11, 2005

(65) Prior Publication Data
US 2006/0013774 A1 Jan. 19, 2006

(30) Foreign Application Priority Data
Mar. 12, 2004 (FR) .................................. 04 02579

(51) Int. Cl.
A61B 5/055 (2006.01)
(52) U.S. Cl. .................. 424/9.363; 424/9.3; 424/9.36; 424/9.361; 424/9.362
(58) Field of Classification Search ............... 424/1.11, 424/1.65, 9.1, 9.3, 9.361, 9.362, 9.36, 9.363; 540/450
See application file for complete search history.

(56) References Cited

U.S. PATENT DOCUMENTS

| | | | |
|---|---|---|---|
| 4,647,447 | A | 3/1987 | Gries et al. |
| 4,804,529 | A | 2/1989 | Bardy et al. |
| 4,986,256 | A | 1/1991 | Cohen et al. |
| 5,169,944 | A | 12/1992 | Nelson et al. |
| 5,236,915 | A | 8/1993 | Fiel |
| 5,262,532 | A | 11/1993 | Tweedle et al. |
| 5,284,647 | A | 2/1994 | Niedballa et al. |
| 5,674,467 | A | 10/1997 | Maier et al. |
| 5,695,739 | A | 12/1997 | Schmitt-Willich et al. |
| 5,712,389 | A | 1/1998 | Meyer et al. |
| 5,980,864 | A | 11/1999 | Platzek et al. |
| 6,123,920 | A | 9/2000 | Gunther et al. |
| 6,187,285 | B1 | 2/2001 | Meyer et al. |
| 6,251,367 | B1 | 6/2001 | Platzek et al. |
| 6,440,956 | B1 | 8/2002 | Port |
| 6,537,520 | B1 | 3/2003 | Rajopadhye et al. |
| 2002/0128472 | A1 | 9/2002 | Platzek et al. |
| 2003/0100752 | A1 | 5/2003 | Robinson |

FOREIGN PATENT DOCUMENTS

| | | |
|---|---|---|
| EP | 0 071 564 A1 | 2/1983 |
| EP | 0 133 603 A1 | 2/1985 |
| EP | 0 203 962 B1 | 12/1986 |
| EP | 0 230 893 A2 | 8/1987 |
| EP | 0 290 047 A2 | 11/1988 |
| EP | 0 292 689 A2 | 11/1988 |
| EP | 0 336 879 A1 | 10/1989 |
| EP | 0 350 948 A2 | 1/1990 |
| EP | 0 405 704 | 1/1991 |
| EP | 0 425 571 B1 | 5/1991 |
| EP | 0 448 191 A1 | 9/1991 |
| EP | 0 661 279 A1 | 7/1995 |
| EP | 0 922 700 A1 | 6/1999 |
| EP | 1 148 057 A1 | 10/2001 |
| EP | 1 183 255 B1 | 3/2002 |
| JP | 11-217385 | 10/1999 |
| WO | WO-86/02841 A1 | 5/1986 |
| WO | WO-90/01024 A1 | 2/1990 |
| WO | WO-94/19352 A1 | 9/1994 |
| WO | WO-95/17910 A2 | 4/1995 |
| WO | WO-95/31219 A1 | 11/1995 |
| WO | WO-02/48119 A2 | 6/2002 |
| WO | WO-03/074523 A2 | 9/2003 |

OTHER PUBLICATIONS

R.J. Fiel et al., *Magnetic Resonance Imaging*, vol. 8, (1990), pp. 255-259. XP000983410.
Rashid Fawwaz et al., *Nucl. Med. Biol.*, vol. 17, No. 10, (1990), pp. 65-72, XP008023293.
Akira Matsumura et al., *Neurol. Med. Chir.*, vol. 37, (1997), pp. 327-331. XP001084819.
Takehara Yasuo et al., *Magnetic Resonance in Medicine*, vol. 47, No. 3, (2002), pp. 549-553. XP002291536.
Schmiedl Up et al., *Investigative Radiology*, vol. 27, No. 7, (1992), pp. 536-542. XP002291537.
David A. Place et al., *Magnetic Resonance Imaging*, vol. 10, No. 6, (1992), pp. 919-928. XP002291538.
S.W. Kim et al., *Nippon Acta Radiologica*, vol. 50, No. 2, (1990), pp. 192-194. XP002291539.
J. Maurer et al., *Der Radiologe*, vol. 39, No. 5, (May 1999), pp. 422-427. XP002291540.
L.J. Wilmes et al., *Journal of Magnetic Resonance Imaging*, vol. 3, No. 1, (Jan. 1993), pp. 5-12. XP002291541.
G. Marchal et al., *European Radiology, Springer International, Berlin*, vol. 6, No. 1, (1996), pp. 2-8. XP009025342.
Polivina Jolicia F. Gauuan et al., *Bioorganic & Medical Chemistry*, vol. 10, (2002), pp. 3013-3021. XP002292093.

*Primary Examiner*—Dameron L. Jones
(74) *Attorney, Agent, or Firm*—Birch, Stewart, Kolasch & Birch, LLP

(57) ABSTRACT

A new use in magnetic resonance imaging employing a field greater than 1.5 Tesla, of a porphyrin compound of the following general formula I is provided:

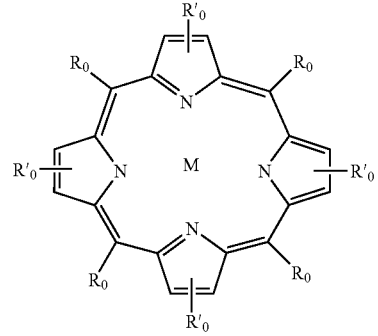

in which $R_0$ and $R'_0$ are such that the compound is soluble in a biological medium, and M denotes a paramagnetic metal ion, advantageously $Mn^{3+}$. The present invention also relates to novel porphyrin compounds.

17 Claims, 1 Drawing Sheet

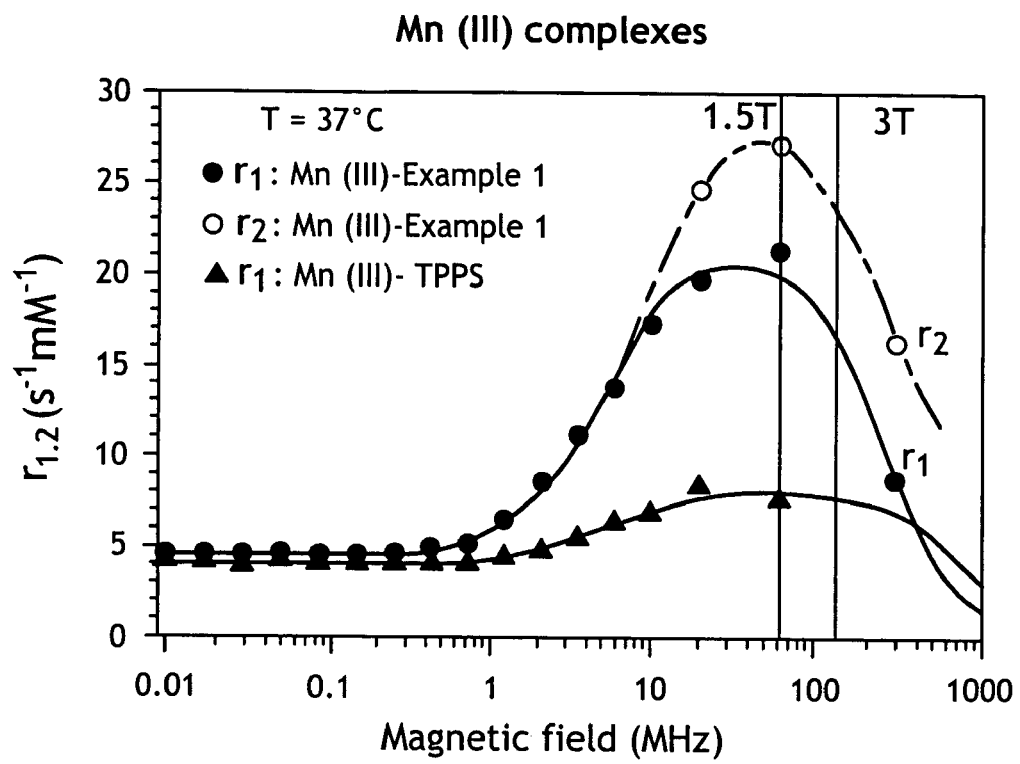
FIG.1 : Experimental relaxivity curves
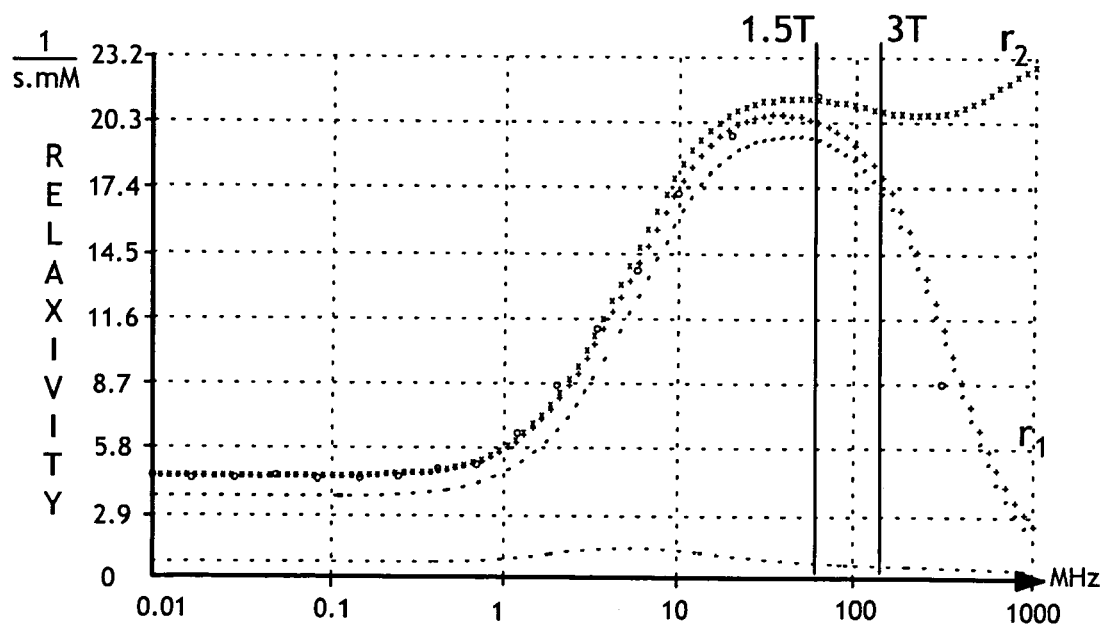
FIG.2 : Theoretical r1, r2 relaxivity curves

PORPHYRIN COMPOUNDS AND THEIR USE IN HIGH-FIELD MRI

The invention relates to the use of compounds in high-field magnetic resonance imaging (MRI). The invention preferably relates to the use, in high-field MRI, of porphyrin compounds, in particular manganese porphyrin compounds, or other compounds which are able to form chelates with manganese.

It may be recalled that MRI consists in applying a magnetic field, resulting in the excitation of water molecules, which return to their initial state after a certain period termed the relaxation period.

The physical quantity measured in MRI is the rate of relaxation, which is the inverse of the relaxation time, of the protons of the water following exposure in the magnetic field. The use of contrast agents alters the relaxation time of the protons of the water, making it possible to markedly improve diagnosis by imaging. The relaxivity (in $s^{-1}$ $mM^{-1}$) denotes the rate of relaxation of a 1 mM concentration of contrast agent. In a general manner, the imaging signal improves as the relaxivity increases.

A large number of chelate-based contrast agents for MRI are known, in particular linear or macrocyclic gadolinium chelates which are described, for example, in the documents EP 71 564, EP 448 191, WO 02/48119, EP 203 962, EP 292 689, EP 425 571, EP 230 893, EP 405 704, EP 290 047, U.S. Pat. No. 6,123,920, EP 292 689, and EP 230 893, for example the compounds diethylenetriaminepentaacetic acid (DTPA), DTPA BMA, DTPA BOPTA, DO3A and 1,4,7,10-tetracyclododecane-N,N',N'',N'''-tetraacetic acid (DOTA).

These are low molecular weight chelates which do not interact with the biological medium. In practice, these agents are used at a magnetic field which is described as being a low field, of the order of from 0.3 to 1 T, in general of 0.5T. The r1 relaxivity of these agents is of the order of from 3 to 5 $mmol^{-1}s^{-1}$ at these fields. While the relaxivity does not decrease very much at a higher field, of the order of 3 T, it remains overall relatively low, typically less than 5 $mmol^{-1}s^{-1}$ (cf. table 3).

The prior art also describes agents which have a higher r1 relaxivity, of at least from 20 to 40 $mmol^{-1}s^{-1}$ at low field (of the order of 0.5 T) and which are currently still at the stage of clinical development, in particular MS325 and compounds of the dendrimer type. However, these compounds suffer from the disadvantage of not having a very satisfactory r1 relaxivity at high field. Thus, their r1 relaxivity follows a Gaussian curve: the r1 relaxivity increases progressively with the field up to 0.5 to 1 T, depending on the chelates, and then drops sharply and rapidly, with the relaxivity not being at all as satisfactory from 1 to 1.5 T onwards (cf. table 2).

However, there exists a real need to have available chelates which give rise to a high r1 relaxivity, with this ideally being at fields which are higher than the fields of from 0.5 to 1.5 T which are at present commonly being used in clinical medicine. The reason for this is that imaging appliances are evolving toward ever higher magnetic fields because increasing the field makes it possible to increase the signal to noise ratio.

It is not possible to carry out MRI imaging without background noise, due, in particular, to an acquisition noise at the level of the imager take-up reel and of the sample itself (electronic and magnetic losses). The signal to noise ratio is defined as the value of the signal emitted in a region of the image weighted by the variability of the signal (standard deviation) in a region where there is not meant to be any signal.

It is established that the signal to noise ratio is proportional to the magnetic field which is applied. It is thus expected that high-field (in particular of the order of 3 T) imaging appliances will be used regularly in the coming years, particularly in order to reduce the dose of contrast agent to be injected, something which is a very useful factor from the economic, clinical and toxicological points of view.

The applicant has surprisingly succeeded in demonstrating that certain chelates exhibit a satisfactory r1 relaxivity even at high fields, with the drop in relaxivity which is expected beyond 1.5 T occurring to a much lesser extent than in the case of compounds having a relaxivity of at least 20 to 40 $mmol^{-1}s^{-1}$ at low field, such as MS325 or the dendrimers. Contrary to what is described and suggested in the prior art, the relaxivity curve is different from that of the chelates which are generally used in MRI. These compounds which are effective at high field are, in particular, chelates of the porphyrin type, in particular manganese porphyrins. Manganese is advantageous because of its high degree of stability and the high magnetic moment of its porphyrin complex.

These porphyrins have the following general formula: (I)

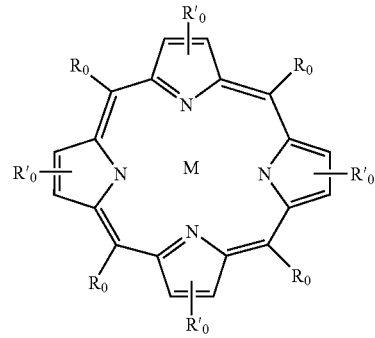

in which the $R_0$s and the $R'_0$s are such that the compound is sufficiently soluble for diagnostic use in MRI, and M denotes a paramagnetic metal ion.

A large number of examples of $R_0$ groups are described in the present application. The $R'_0$s can be absent.

The invention thus relates, according to a first aspect, to the use, in MRI at a field higher than 1.5 Tesla, of porphyrin compounds of the following general formula (I):

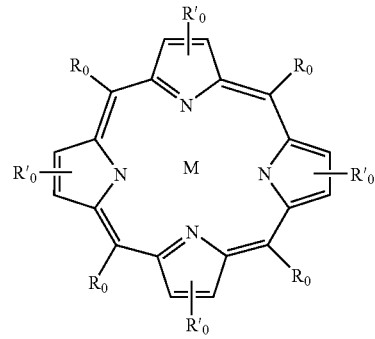

in which $R_O$ and $R'_O$ are such that the compound is soluble in a biological medium and M denotes a paramagnetic metal ion.

Paramagnetic metals which may be mentioned are manganese, chromium, iron, cobalt, nickel, copper, gadolinium and dysprosium. Advantageously, the paramagnetic metal is $Mn^{3+}$.

Within the meaning of the present invention, "biological medium" is understood as being that which is met with during with clinical examinations, namely, and in particular, plasma, blood and biological fluids from healthy or diseased tissues.

These porphyrin compounds are effective at high field. Within the meaning of the present invention, "compound which is effective at high field" is understood as being any compound for which the r1 relaxivity is satisfactory at high field. Advantageously, these compounds have a favourable r2/r1 ratio, that is to say advantageously less than 2, advantageously between 1.1 and 1.5. Within the meaning of the present invention, "high field" is understood as being any magnetic field starting with which the relaxivity of the compounds of the prior art falls in a manner which is such that using them is disadvantageous. Thus, high fields commonly correspond, for the skilled person, to values higher than the range [1; 1.5 T] (range beyond which the prior art teaches that the relaxivity curve decreases in the case of the majority of the chelates known to the skilled person, with the decrease being particularly sharp in the case of the chelates which have a high r1 relaxivity at low fields, advantageously greater than 1.5 T). Advantageously, the high fields are typically of the order of from 2 to 7 T, of from 3 to 7 T, if not from 2 to 4 T or from 3 to 4 T or more. However, this value of 1.5 T is not a strict value, with the fall in relaxivity being able to be more or less sharp depending on the chelates. The advantageous compounds are such that their r1 relaxivity at high field (of the order of 3 T) is preferably at least 60%, more preferably at least 75%, of their relaxivity at low field (of the order of 0.5 T).

Advantageously, their r1 relaxivity, as measured at a field higher than 1.5 T, is between 10 and 300 $mmol^{-1}s^{-1}$, advantageously between 10 and 50 $mmol^{-1}s^{-1}$. Within the meaning of the present invention, the term "soluble" is understood as meaning that the compound exhibits a biological medium solubility which is sufficient for diagnostic use in MRI. The desirable solubility is advantageously at least 1 mM/l.

As will be detailed below, the applicant has obtained very satisfactory results using a porphyrin compound of the TPPS4 type. However, the invention is not limited to these compounds; it covers the use of any porphyrin compound of the general formula I, in particular of the formulae (II) to (VI) described below.

According to one embodiment, the compounds which can be used in accordance with the present invention have the formula (II):

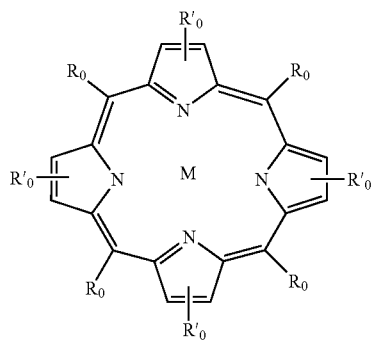

in which M denotes a paramagnetic metal ion, advantageously $Mn^{3+}$, and $R_O$ denotes:

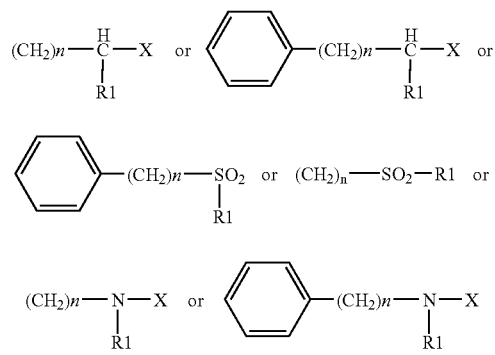

in which:

n is an integer between 0 and 8, each X, identical or different, denotes a hydrogen atom or a $COR_a$, $SO_3R_e$, $CO_2R_a$, $CONR_bR_c$ or $P(R_d)OOH$ group in which $R_a$, $R_b$, $R_c$ and $R_e$, identical or different, respectively denote a hydrogen atom or an optionally hydroxylated ($C_1$-$C_8$) alkyl group; P denotes the phosphorus atom and $R_d$ denotes an OH group or a ($C_1$-$C_8$) alkyl or ($C_1$-$C_8$) alkoxy group;

each R1 identical or different, denotes a hydrogen atom or a hydrophilic group which comprises at least three oxygen atoms whose molecular weight is greater than 200 g/mol, advantageously at least 400 g/mol, advantageously at least 500 g/mol, advantageously at least 700 g/mol, advantageously at least 800 g/mol, advantageously at least 1000 g/mol, advantageously at least 1500 g/mol, and which is selected from the group consisting of:

a polyoxy($C_2$-$C_3$)alkylene group (i.e. polyoxyethylenes or polyoxypropylenes); this group is advantageously polyethylene glycol or its $C_1$ to $C_3$ monoethers or monoesters, having a molecular mass which is advantageously between 1000 and 2000 g/mol;

a polyhydroxyalkyl a polyol (advantageously of the functionalized oligosaccharide type (this type of functionalization being described, in particular, in J. Polymer. Sc. Part A Polymer chemistry 23 1395-1405 (1985) and 29, 1271-1279 (1991) and in Bioconjugate chem. 3, 154-159 (1992))

a group of the formula $(R_2G)_e[(R_2G)_iR_3]_h$, in which:
h=1 or 2;
i=0, 1 or 2;
e=1 to 5 the $R_2$s, which are identical or different, are absent or denote a $C_1$ to $C_{14}$ alkylene group; $C_1$ to $C_{14}$ alkoxyalkylene, $C_1$ to $C_{14}$ polyalkoxyalkylene; a phenylene or a saturated or unsaturated heterocyclic group, optionally substituted by OH, Cl, Br, I, or a $(C_1$-$C_8)$alkyl, $(C_1$-$C_8)$alkyloxy, $NO_2$, $NR_XR_Y$, $NR_XCOR_Y$, $CONR_XR_Y$ or $COOR_X$ group in which $R_X$ and $R_Y$ denote, independently of each other, H or a $(C_1$-$C_8)$alkyl group, with the alkyl, alkylene and alkoxy groups being linear, branched or cyclic and being able to be hydroxylated;
the Gs, identical or different, are absent or denote an oxygen atom or a CO, OCO, COO, $SO_3$, $OSO_2$, CONR', NR'CO, NR'COO, OCONR', NR', NR'CS, CSNR', $SO_2$NR', NR'$SO_2$, NR'CSO, OCSNR', NR'CSNR', P(O) (OH)NR' or NR'P(O)—(OH) group in which R' denotes H, a $(C_1$-$C_8)$alkyl group or $R_3$; $R_3$ denotes a $(C_1$-$C_{14})$alkyl group; a phenyl group; a $C_1$-$C_{14}$ alkyl group which is substituted or interrupted by (a) phenyl group(s); a $C_1$-$C_{14}$ alkyleneoxy group; an amino or amido group which is unsubstituted or substituted by a $C_1$-$C_{14}$ alkyl group optionally substituted or interrupted by one of the preceding groups; with the phenyl, phenylene and heterocyclic groups being able to be substituted by OH, Cl, BR, I, or a $(C_1$-$C_8)$alkyl, $(C_1$-$C_8)$alkoxy, $NO_2$, $NR_XR_Y$, $NR_XCOR_Y$, $CONR_XR_Y$ or $COOR_X$ group in which $R_X$ and $R_Y$ denote, independently of each other, H or a $(C_1$-$C_8)$alkyl group, with the alkyl, alkylene and alkoxy groups being linear, branched or cyclic and being able to be hydroxylated;

on condition that X and R1 do not simultaneously denote a hydrogen atom.

Advantageously, R1 corresponds to the formula $R_2GR_3$ in which:

$R_2$ is absent or denotes a linear, branched or cyclic $C_1$-$C_{14}$ alkylene group; linear, branched or cyclic $C_1$-$C_{14}$ alkoxyalkylene; linear, branched or cyclic $C_1$-$C_{14}$ polyalkoxyalkylene; a phenylene or a saturated or unsaturated heterocyclic group which are optionally substituted by OH, Cl, Br, I or a linear, branched or cyclic $(C_1$-$C_8)$alkyl, linear, branched or cyclic $(C_1$-$C_8)$alkoxy, $NO_2$, $NR_XR_Y$, $NR_XCOR_Y$, $CONR_XR_Y$ or $COOR_X$ group in which $R_X$ and $R_Y$ denote a hydrogen atom or a linear, branched or cyclic $(C_1$-$C_8)$alkyl group, with the alkyl, alkylene, alkoxy, polyalkoxyalkylene and alkoxyalkylene groups being able to be hydroxylated;

G is absent or denotes an oxygen atom or a CO, OCO, COO, $SO_3$, $OSO_2$, CONR', NR'CO, NR'COO, OCONR', NR', NR'CS, CSNR', $SO_2$NR', NR'$SO_2$, NR'CSO, OCSNR', NR'CSNR', P(O)(OH)NR' or NR'P(O)—(OH) group in which R' denotes a hydrogen atom H, a $(C_1$-$C_8)$alkyl group or $R_3$;

$R_3$ denotes a $C_3$-$C_{14}$ alkyl group; a phenyl group; a $C_1$-$C_{14}$ alkyl group which is substituted, or interrupted, by (a) phenyl group(s); a $C_1$-$C_{14}$ alkyleneoxy group; an amino or amido group which is unsubstituted or substituted by a $C_1$-$C_{14}$ alkyl group optionally substituted or interrupted by one of the preceding groups; or $R_3$ denotes a compound which is optionally monofunctionalized and which is selected from saccharides and oligosaccharides, or phenyl, phenylene and heterocyclic groups which can be substituted by OH, Cl, Br or I or a $(C_1$-$C_8)$alkyl, $(C_1$-$C_8)$alkoxy, $NO_2$, $NR_XR_Y$, $NR_XCOR_Y$, $CONR_XR_Y$ or $COOR_X$ group in which $R_X$ and $R_Y$ denote, independently of each other, H or a $(C_1$-$C_8)$alkyl group, with the alkyl, alkylene and alkoxy groups being linear, branched or cyclic and being able to be hydroxylated;

According to one embodiment, the porphyrin compounds which can be used within the context of the present invention are porphyrins of the tetraphenylporphyrin type, in particular mesotetraphenylporphyrins of the following formula (III)

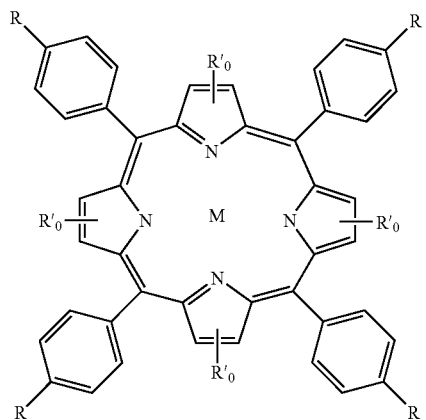

in which M denotes a paramagnetic metal ion, advantageously $Mn^{3+}$, which are, in particular, described and exemplified in the documents U.S. Pat. No. 5,674,467, U.S. Pat. No. 5,284,647, EP 336 879, JP 11217385, U.S. Pat. No. 5,674,467 and U.S. Pat. No. 5,262,532, which are hereby incorporated by reference. These compounds are, in particular, compounds of claim 1 in the U.S. Pat. No. 5,284,647 and U.S. Pat. No. 5,674,467, in particular 1) the compounds for which R denotes R8 or R9 with R8 denoting a group of the general formula —(O)$_s$—(CH$_2$)$_k$—X—CH$_2$—Y—C=O)-Z in which s is 0 or 1;

k is 0, 1, 2 or 3;

X is O, a bond or NR10; R10 is $C_1$-$C_4$ acyl, $C_1$-$C_{10}$ alkylsulfonyl, benzenesulfonyl, $C_1$-$C_4$ alkylphenylenesulfonyl, carboxy-$C_1$-$C_6$ alkyl or carboxy-$C_1$-$C_5$ acyl;

Y is a bond or —CHOH; Z-OH or —NR11R12; R11 and R12 are, independently, H or a saturated or unsaturated, linear or branched chain comprising up to 16 carbon atoms which is optionally substituted by from 1 to 6 hydroxyl groups, with R9 being H, F, Cl, Br, I, a linear or branched $C_1$-$C_4$ alkyl chain or a group of the formula —(O)$_s$—(CH$_2$)$_k$—X—CH$_2$—Y—C=O)-Z 2) the compounds for which R denotes CO-A, $SO_2$-A, OR5, R5, W or NH—W; in which A is OH, OR4, NR5R6 or —(NH)$_x$-{Q-(NH)$_y$}$_w$—W;

R4 is $C_1$-$C_6$ alkyl or benzyl;

R5 and R6 are, independently, H or a linear or branched, saturated or unsaturated $C_1$-$C_{16}$ chain which is optionally substituted by one or more hydroxyl or $C_1$-$C_6$ alkoxy groups, or, when R6 is H, R5 can be a $C_6$-$C_{10}$ aryl or a $C_1$-$C_6$ alkyl, Or R5 and R6 form, together with a nitrogen atom, a saturated or unsaturated cycle, x and y are in each case, independently, 0, 1 or 2; w is 0 or 1;

Q is $C_1$-$C_{20}$ alkylene;

W is H or V—H with V being a bond or a cyclic, aliphatic or aromatic, linear or branched, hydrocarbon chain comprising up to 20 C atoms and including, in particular, —NH—, —O—, —S—, —N—, —CO—O—, —O—CO—, (OCH$_2$CH$_2$—), —NH—CO—, —CO—NH—, —NH—NH—, —$C_6H_4$—NH—, —$C_6H_4$—O— and —$C_6H_4$—.

Advantageously, the R'$_0$s according to the present invention are identical to the R3 groups which are defined in the document U.S. Pat. No. 5,674,467; advantageously, R'$_0$ denotes H or a linear or branched $C_1$-$C_4$ alkyl group.

According to one embodiment of the invention, the porphyrin compounds which can be used within the context of the present invention are manganese porphyrins of the formula (III) in which M denotes $Mn^{3+}$, R denotes $SO_3H$ and R'$_0$ is absent. These compounds, whose relaxivity is in the vicinity of 10 mMol$^{-1}$s$^{-1}$, are termed Mn TPPS4 (compound IIIa).

According to another embodiment of the invention, the porphyrin compounds which can be used within the context of the present invention are manganese porphyrins of the formula (III) in which M denotes $Mn^{3+}$, R denotes $CO_2H$ and R'$_0$ is absent. These compounds, whose relaxivity is in the vicinity of 10 mMol$^{-1}$s$^{-1}$, are termed Mn TCPP4 (compound IIIb).

The chelates MnTPPS4 and MnTCPP4 are described, in particular, in R. J. Field, Magnetic Resonance Imaging, vol 5-149-156, 1987; R. C. Brasch, radiology, 1992, 183, 1-11; G. A. Mercier, Magnetic Resonance Imaging, 807-817, 1995, and WO 95/31219. Their use in the prior art is limited to low fields, less than 1 T. The relaxivity of MnTPPS4 is 10.7 and 12.2 mMol$^{-1}$s$^{-1}$, respectively, in blood plasma at 0.25 T and 17 mMol$^{-1}$s$^{-1}$ at 1.5 T. This relaxivity is relatively high as compared with that of DOTA or of DTPA (relaxivity of the order of from 3 to 5 mmol$^{-1}$s$^{-1}$).

The sulfonate groups improve the solubility in aqueous medium (solubility of MnTPPS4=20 mg/ml, pH=7, 0.9% NaCl).

The use of carboxylate improves the relaxivity (solubility of MnTCPP4=1 mg/ml, pH=7, 0.9% NaCl).

According to one embodiment of the present invention, the compounds (III) are such as defined in the U.S. Pat. No. 5,262,532, with, advantageously, R=CON(CH$_2$OH)$_2$ (r1 relaxivity=12 mMol$^{-1}$s$^{-1}$ at 1 T) or R=CONHCH$_2$CHOHCH$_2$OH (r1=25 mMol$^{-1}$s$^{-1}$ at 1 T).

According to another particularly advantageous embodiment of the present invention, the porphyrin compounds which can be used within the context of the present invention are manganese porphyrins of the following formula (IV)

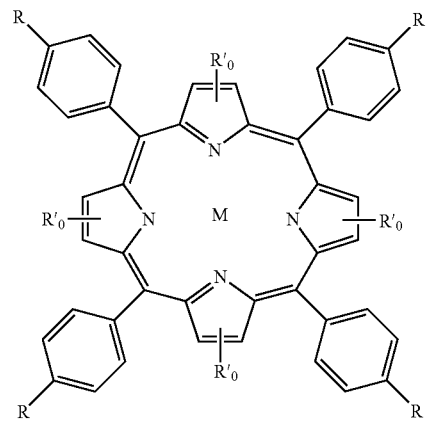

in which M denotes a paramagnetic metal ion, advantageously $Mn^{3+}$, R'$_0$ is absent and R denotes:

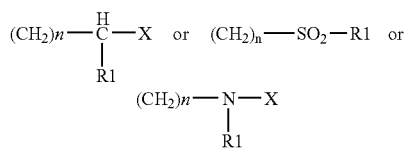

in which n is an integer between 0 and 8, each X is identical or different and denotes a hydrogen atom or a $COR_a$, $SO_3R_e$, $CO_2R_a$, $CONR_bR_c$ or $P(R_d)OOH$ group in which $R_a$, $R_b$, $R_c$ and $R_e$ are identical or different and respectively denote a hydrogen atom or an optionally hydroxylated ($C_1$-$C_8$) alkyl group; P denotes the phosphorus atom, and Rd denotes an OH group or a ($C_1$-$C_8$) alkyl or ($C_1$-$C_8$)alkoxy group;

each R1 is identical or different and denotes a hydrogen atom or a hydrophilic group which comprises at least three oxygen atoms, whose molecular weight is greater than 200 g/mol, advantageously at least 400 g/mol, advantageously at least 500 g/mol, advantageously at least 700 g/mol, advantageously at least 800 g/mol, advantageously at least 1000 g/mol and advantageously at least 1500 g/mol and which is selected from the group consisting of:

a polyoxy($C_2$-$C_3$)alkylene group (i.e. polyoxyethylenes or polyoxypropylenes); advantageously, the group is polyethylene glycol, or its $C_1$ to $C_3$ monoethers or monoesters, advantageously having a molecular mass of between 1000 and 2000 g/mol;

a polyhydroxyalkyl a polyol, advantageously of the functionalized oligosaccharide type a group of the formula $(R_2G)_e[(R_2G)_iR_3]_h$ in which:

h=1 or 2;

i=0, 1 or 2;

e=1 to 5 the $R_2$s, which are identical or different, are absent or denote a $C_1$ to $C_{14}$ alkylene group; $C_1$ to $C_{14}$ alkoxyalkylene, $C_1$ to $C_{14}$ polyalkoxyalkylene; a phenylene or a saturated or unsaturated heterocyclic group which are optionally substituted by OH, Cl, Br, I or a ($C_1$-$C_8$)alkyl, ($C_1$-$C_8$)alkoxy, $NO_2$, $NR_XR_Y$, $NR_XCOR_Y$, $CONR_XR_Y$ or $COOR_X$ group in which $R_X$ and $R_Y$ denote, independently of each other, H or a ($C_1$-$C_8$)alkyl group, with the alkyl, alkylene and alkoxy groups being linear, branched or cyclic and being able to be hydroxylated;

the Gs, which are identical or different, are absent or denote an oxygen atom or a CO, OCO, COO, $SO_3$, $OSO_2$, CONR', NR'CO, NR'COO, OCONR', NR', NR'CS, CSNR', $SO_2NR'$, $NR'SO_2$, NR'CSO, OCSNR', NR'CSNR', P(O) (OH)NR' or NR'P(O)—(OH) group in which R' denotes H, a ($C_1$-$C_8$)alkyl group or $R_3$;

$R_3$ denotes a $C_1$-$C_{14}$ alkyl group; a phenyl group; a $C_1$-$C_{14}$ alkyl group which is substituted, or interrupted, by (a) phenyl group(s); a $C_1$-$C_{14}$ alkyleneoxy group; an amino or amido group, unsubstituted or substituted by a $C_1$-$C_{14}$ alkyl group which is optionally substituted, or interrupted, by one of the preceding groups; with it being possible for the phenyl, phenylene and heterocyclic groups to be substituted by OH, Cl, Br, I or a ($C_1$-$C_8$)alkyl, ($C_1$-$C_8$) alkoxy, $NO_2$, $NR_XR_Y$, $NR_XCOR_Y$, $CONR_XR_Y$ or $COOR_X$ group in which $R_X$ and $R_Y$ denote, independently of each other, H or a ($C_1$-$C_8$)alkyl group, with the alkyl, alkylene and alkoxy groups being linear, branched or cyclic and being able to be hydroxylated;

on condition that X and R1 do not simultaneously denote a hydrogen atom.

Advantageously, R1 corresponds to the formula $R_2GR_3$ in which:

$R_2$ is absent or denotes a linear, branched or cyclic $C_1$-$C_{14}$ alkylene group; linear branched or cyclic $C_1$-$C_{14}$ alkoxyalkylene; linear, branched or cyclic $C_1$-$C_{14}$ polyalkoxyalkylene; a phenylene or a saturated or unsaturated heterocyclic group which are optionally substituted by OH, Cl, Br, I or a linear, branched or cyclic ($C_1$-$C_8$)alkyl, linear, branched or cyclic ($C_1$-$C_8$)alkoxy, $NO_2$, $NR_XR_Y$, $NR_XCOR_Y$, $CONR_XR_Y$ or $COOR_X$ group in which $R_X$ And $R_Y$ denote a hydrogen atom or a linear, branched or cyclic ($C_1$-$C_8$)alkyl group, with the alkyl, alkylene, alkoxy, alkoxylakylene and polyalkoxyalkylene groups being able to be hydroxylated;

G is absent or denotes an oxygen atom or a CO, OCO, COO, $SO_3$, $OSO_2$, CONR', NR'CO, NR'COO, OCONR', NR', NR'CS, CSNR', $SO_2NR'$, $NR'SO_2$, NR'CSO, OCSNR', NR'CSNR', P(O)(OH)NR' or NR'P(O)—(OH) group in which R' denotes a hydrogen atom H, a ($C_1$-$C_8$)alkyl group or $R_3$;

$R_3$ denotes a $C_1$-$C_{14}$ alkyl group; a phenyl group; a $C_1$-$C_{14}$ alkyl group which is substituted, or interrupted, by (a) phenyl group(s); a $C_1$-$C_{14}$ alkyleneoxy group; an amino or amido group unsubstituted or substituted by a $C_1$-$C_{14}$ alkyl group which is optionally substituted, or interrupted, by one of the preceding groups; or $R_3$ denotes a compound which may optionally be monofunctionalized and which is selected from saccharides and oligosaccharides, with the phenyl, phenylene and heterocyclic groups being able to be substituted by OH, Cl, Br, I or a ($C_1$-$C_8$)alkyl, ($C_1$-$C_8$)alkoxy, $NO_2$, $NR_XR_Y$, $NR_XCOR_Y$, $CONR_XR_Y$ or $COOR_X$ group in which $R_X$ and $R_Y$ denote, independently of each other, H or a ($C_1$-$C_8$)alkyl group, with the alkyl, alkylene and alkoxy groups being linear, branched or cyclic and being able to be hydroxylated.

The present invention also relates to the compounds of the formula IV as such.

These novel compounds of the formula (IV), which have been prepared by the applicant, have a high relaxivity, i.e. of the order of from 15 to 30 mmol$^{-1}$s$^{-1}$ at 1 T depending on the X and R1 groups which are selected. This high relaxivity makes it possible to improve the signal and, where appropriate, avoid possible problems of toxicity: the fact that the manganese porphyrin has a higher relaxivity per mole means that an identical signal can be obtained while reducing the dose of the manganese porphyrin which is administered. Thus, it may be recalled that the porphyrin group is able to give rise to undesirable phototoxic reactions. Furthermore, by increasing the hydrophilicity, these X and R1 groups confer good solubility on the compounds of the formula (IV).

According to an advantageous embodiment, the compounds of formula (IV) which can be used within the context of the present invention are such that R1 denotes $(CH_2)_xCONHR_h$, in which x=1, 2 or 3 and Rh is a hydrophilic group which has a molecular weight greater than 200 g/mol and which is selected from:

1) a group:

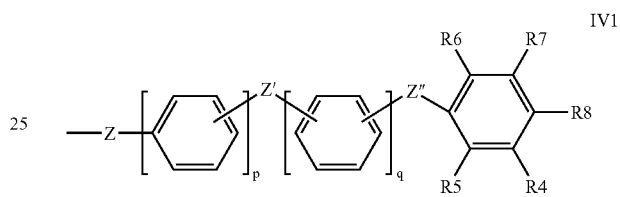

in which

Z denotes a bond or a $CH_2$, $CH_2CONH$ or $(CH_2)_2NHCO$ group

Z' denotes a bond, an atom of oxygen or sulfur, or a NQ, $CH_2$, CO, CONQ, NQCO, NQ-CONQ or $CONQCH_2CONQ$ group, Z" denotes a bond or a CONQ, NQCO or $CONQCH_2CONQ$ group p and q are integers such that p+q is between 0 and 3;

$R_4$, $R_5$, $R_6$, $R_7$ and $R_8$ denote:

either, independently of each other, H, Br, Cl, I, $CONQ_1Q_2$ or $NQ_1COQ_2$ in which $Q_1$ and $Q_2$, which are identical or different, denote H or a ($C_1$-$C_8$)alkyl group which is monohydroxylated or polyhydroxylated or optionally interrupted by (a) atom(s) of oxygen, and at least one and at most two of $R_4$ to $R_8$ denote(s) a $CONQ_1Q_2$ or $NQ_1COQ_2$ group;

or $R_7$ and $R_4$ denote a group of the formula

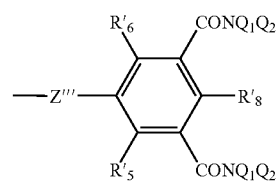

in which $R_6$, $R'_6$, $R_8$, $R'_8$, $R_5$ and $R'_5$, which are identical or different, denote H, Br, Cl or I, $Q_1$ and $Q_2$ are as defined above and Z''' denotes a group selected from CONQ, $CONQCH_2CONQ$, $CONQCH_2$, $NQCONQ$ or $CONQ (CH_2)_2NQCO$, Q denotes H or an optionally hydroxylated ($C_1$-$C_4$)alkyl group, with the alkyl groups being able to be linear or branched;

2) a "flash" branch of the formula

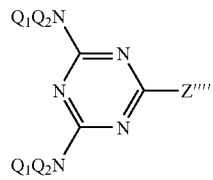

in which

Z"" denotes a group of the formula $NQ(CH_2)_j(CH_2OCH_2)_i(CH_2)_jNH_2$ in which i=0 to 6 and j=1 to 6 and Q is as defined above, $Q_1$ and $Q_2$ are as defined above.

Advantageously, the "flash" branch is selected from the group consisting of

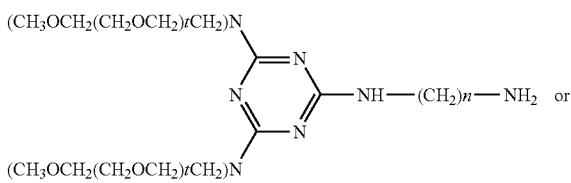

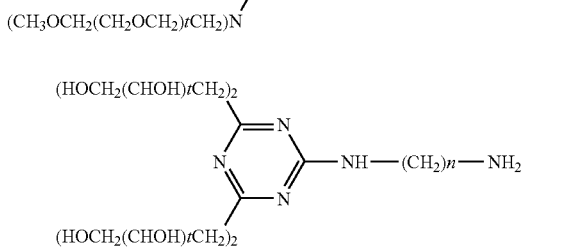

in which t=1, 2, 3 or 4 and n=2 to 6.

According to an advantageous embodiment, the compounds of formula (IV) which can be used within the context of the present invention are such that R1 denotes:

a group of the formula

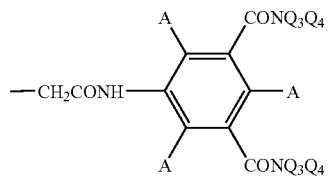

in which
the As are identical and denote Br or I, and
$Q_3$ and $Q_4$, which are identical or different, denote a ($C_1$-$C_8$)alkyl group which is monohydroxylated or polyhydroxylated such that each $CONQ_3Q_4$ comprises from 4 to 10 hydroxyl groups in total a group of the formula

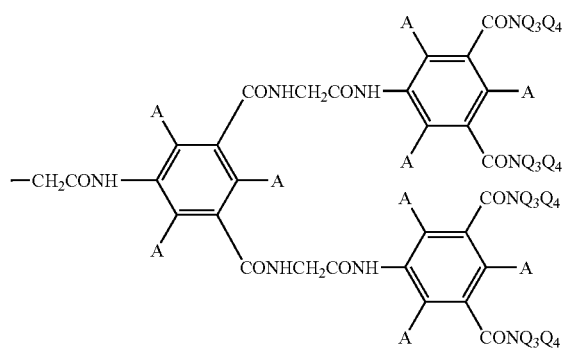

in which
A, $Q_3$ and $Q_4$ are defined as above a group of the formula

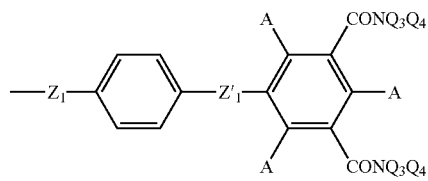

in which
A, $Q_3$ and $Q_4$ are as defined above
$Z_1$ denotes a $CH_2$ or $CH_2CONH$ group,
$Z'_1$ denotes a CONH or $CONHCH_2CONH$ group,
a group of the formula

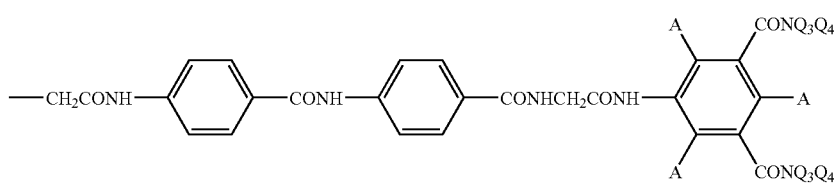

in which
A, $Q_3$ and $Q_4$ are as defined above.

Advantageously, the compound is

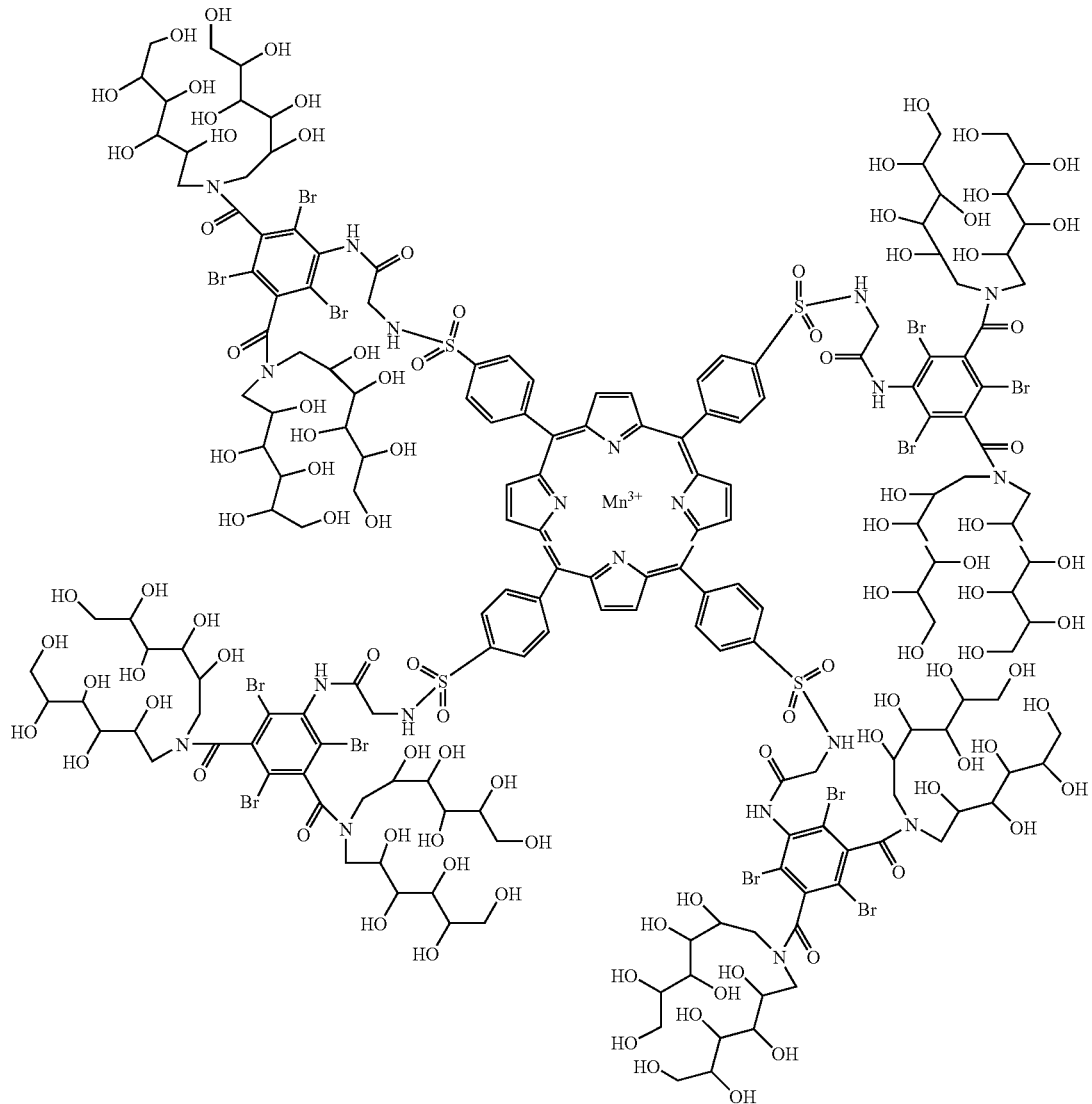

Advantageously, the R1 groups of the compounds of the formula (IV) denote hydrophilic branches as described in the granted patents EP 661 279, EP 922 700 and EP 1 183 255 and their equivalent American patents.

According to other embodiments (V), the porphyrin compounds are as described in the documents EP 1 148 057 (nitroimidazole group carriers), US 2003100752 and U.S. Pat. No. 6,251,367 (substituted deuteroporphyrins coupled to complexing agents of the chelate type for the purpose of detecting necroses and infarction of the myocardium).

In addition, the pyrrole cycles of the compounds (I) to (VI) can be substituted as described, for example, in U.S. Pat. No. 5,674,467 or U.S. Pat. No. 6,251,367.

Among all the compounds of the formulae (I) to (VI) which can be used within the context of the present invention, preference will be given to the compounds which are satisfactory not only in terms of relaxivity but also in terms of stability, solubility and toxicology, in particular to the porphyrin compounds which are described in detail in the cited prior rights and to their functional equivalents.

"Equivalent" is understood as meaning compounds which are not described in detail in these documents but which have a similar chemical structure and exhibit a relaxivity which is similar or greater and which can be measured using the appropriate equipment.

Of all the porphyrin compounds which are mentioned above and which can be used within the context of the present invention, those for which the r2/r1 ratio is close to 1, in particular between 1 and 2, advantageously between 1.1 and 1.5 and therefore close to 1, which is the most desirable for the MRI, will advantageously be selected. Without entering into the details of the physics of the signal, it may be recalled that, for a given magnetic field, the signal which is measured comprises a component termed T1 (where r1=1/T1) and a component termed T2 (r2=1/T2). In order to obtain a satisfactory measure of the signal in T1, which is preferred by the radiologists who use the appliances in clinical medicine, low T1 values and high T2 values (with r1 therefore being large and r2 being low) are sought in the knowledge that T1 is always>T2 (in theory the ideal ratio would be 1). An r2/r1 ratio close to 1 makes it possible to limit the T2 and T2* (susceptibility) effects and thus improve the signal in T1. At 3 Teslas, the r2/r1 ratio is approximately 3.5 T in the case of the compound of example 1.

BRIEF DESCRIPTION OF THE DRAWINGS

Other objects and advantages of the invention will be understood by referring to FIGS. 1 and 2 in which
FIG. 1 depicts:
the r1 curve plotted against the magnetic field using a porphyrin compound according to example 1
the r2 curve plotted against the magnetic field using a porphyrin compound according to example 1
FIG. 2 depicts the r1 and r2 curves, plotted against the magnetic field, which are expected in accordance with the teaching of the prior art.

In a manner which is totally unexpected, the r2 relaxivity which is measured in the case of the compounds of example 1 increases markedly less than anticipated in the case of the high fields, with this making it possible to obtain an r2/r1 ratio less than 2 and therefore a very satisfactory signal in T1 even at high field.

The applicant has thus identified compounds which combine two significant advantages:
a satisfactory relaxivity at high field which is typically greater than 10 mmol$^{-1}$s$^{-1}$
an r2/r1 ratio of the order of from 1.1 to 2, thereby permitting good imaging in T1.

It may be recalled that:
while the previous compounds of the DOTA or DTPA type had a relatively satisfactory r2/r1 ratio at high field (close to 2), they had a low r1 relaxivity (of the order of 5 mmol$^{-1}$s$^{-1}$).
while the previous compounds of the dendrimer or MS325 type, having high r1 relaxivity at low field (of the order of 20 to 40 mmol$^{-1}$s$^{-1}$), had an r1 relaxivity at high field which could be satisfactory (of the order of from 10 to 20 mmol$^{-1}$s$^{-1}$), they had an r2/r1 ratio which was far too unfavorable for T1 imaging.

The r1 and r2 relaxivities, and the r2/r1 ratio, for different field values and different agents are compiled in tables 1 to 3 below:

TABLE 1

Porphyrin compound prepared in accordance with example 1

| Field in Tesla | r1 | r2 | r2/r1 |
|---|---|---|---|
| 1.43 | 21.3 | 27 | 1.28 |
| 3 | 17 | 23 | 1.35 |
| 7 | 8.7 | 16.2 | 2 |

TABLE 2

Compounds of the prior art of the MS325 or dendrimer type

| Field in Tesla | r1 | r2 | r2/r1 |
|---|---|---|---|
| 1.43 | 24 | 49 | 2 |
| 3 | 13 | 68 | 5.2 |
| 7 | 5 | 62 | 12.4 |

TABLE 3

Compounds of the prior art of the DOTA or DTPA type

| Field in Tesla | r1 | r2 | r2/r1 |
|---|---|---|---|
| 3 | 3-5 | 8-10 | 2 |

In the case of the compounds studied by the applicant, the field values which are preferred are of the order of 3 T and 4.7 T (the appliances which are most promising clinically).

The invention also relates to a process for producing a compound of the formula (IV) which can be used at high field, with the process comprising coupling at least three hydrophilic groups R1, as previously described, to a porphyrin nucleus.

Advantageously, the process according to the present invention comprises the steps of complexing a porphyrin with a paramagnetic metal ion M, advantageously Mn$^{3+}$, and oxidizing, chlorinating and amidating the resulting complex in order to obtain a porphyrin compound of the general formula IV.

The invention also relates to:
a diagnostic composition which can be used at high field and which comprises a compound of the formula (IV) and a pharmaceutically acceptable excipient,
a high-field diagnostic method which comprises administering, to a patient, an effective pharmaceutically acceptable dose of a manganese porphyrin compound of the formula IV,
a method for following up a photodynamic therapy by means of diagnostic MRI, comprising administering a paramagnetic photodynamic agent and a compound according to the invention in combination, irradiating said agent and following up the therapy by means of high-field MRI.

The administration procedures which can be used for compounds (I) to (VI) are, for example, as described in the documents U.S. Pat. No. 5,262,532 and U.S. Pat. No. 5,284,647. The pharmaceutically acceptable administration dose of a compound of the formulae (I) to (IV) will advantageously be between 0.01 and 0.5 mmol/kg, advantageously between 0.02 and 0.3 mmol/kg. Where appropriate, use will also be made of agents which are intended to reduce any possible toxicity of the manganese.

The high-field MRI imaging appliances are known to the skilled person.

According to an advantageous embodiment of the invention, the compounds (I) to (VI) will be used for the MRI of cancers, in view of the ability of the metalloporphyrins of the formulae (I) to (VI) to target tumors. Thus, use will advantageously be made of the compounds of the formulae (I) to (IV) according to the present invention which specifically target a cancerous tissue.

It will be possible to seek to increase still further the specificity of the specific targeting of tumors by using groups which are appropriate for targeting a tumor. Use will be made, for example, of sugars which are coupled to the porphyrin nucleus. It will furthermore be possible to combine a diagnostic agent of the formulae (I) to (VI) with at least one therapeutic agent, in particular an anticancerous agent, for example a water-soluble mesosubstituted metalloporphyrin such as Fe(III)T4 MpyP.

However, not all the metalloporphyrins do in fact specifically and/or uniquely target tumors. The invention is not, therefore, limited to using the compounds of the formulae (I) to (VI) for diagnosing cancers. By virtue of their efficacy in terms of a signal, they will also be used for diagnostic indications which are analogous or identical to those of the other, nonspecific, contrast agents, in particular the gadolinium chelates DOTA or DTPA and derivatives. Angiography and perfusion may be mentioned in particular.

A pharmaceutically acceptable dose refers to a dose which is appropriate for a therapeutic or diagnostic use.

Within the meaning of the present invention, "$C_1$-$C_{14}$ alkyl" is understood as being any saturated $C_1$-$C_{14}$ aliphatic hydrocarbon group. The $C_1$-$C_{14}$ alkyls include the $C_1$, $C_2$, $C_3$, $C_4$, $C_5$, $C_6$, $C_7$, $C_8$, $C_9$, $C_{10}$, $C_{11}$, $C_{12}$, $C_{13}$ and $C_{14}$ alkyl groups, for example: methyl, ethyl, n-propyl, i-propyl, n-butyl, s-butyl, t-butyl and n-pentyl.

Within the meaning of the present invention, "$C_1$-$C_8$ alkyl" is understood as being any saturated $C_1$-$C_8$ aliphatic hydrocarbon group. The $C_1$-$C_8$ alkyls include the $C_1$, $C_2$, $C_3$, $C_4$, $C_5$, $C_6$, $C_7$ and $C_8$ alkyl groups, for example: methyl, ethyl, n-propyl, i-propyl, n-butyl, s-butyl, t-butyl and n-pentyl.

Within the meaning of the present invention, "$C_1$-$C_{14}$ alkylene" is understood as being any linear or branched $C_1$-$C_{14}$ hydrocarbon chain comprising at least one double bond, such as methylene, ethylene and 2-methyl-propylene. Within the meaning of the present invention, the term "polyoxyalkylene" advantageously refers to compounds such as polyoxyethylene or polyoxypropylene.

The alkoxy groups include, in particular: methoxy, ethoxy, n-propoxy, i-propoxy, n-butoxy, s-butoxy, t-butoxy, n-pentoxy and s-pentoxy.

Within the meaning of the present invention, "$C_1$-$C_{14}$ alkoxyalkylene" is understood as being any alkoxy as defined above which is linked to an alkylene as defined above.

The cycloalkyls or cyclic alkyls include, in particular: cyclopropyl, cyclobutyl and cyclopentyl.

The heterocycles include, in particular, those mentioned in the U.S. Pat. No. 6,537,520, in particular: pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl and isatinoyl.

Other objects and advantages of the invention will be understood from reading the detailed examples which follow. The examples are given by way of indication and not by way of limitation.

A large number of examples of hydrophilic R1 groups are described in detail in the documents EP 661 279, EP 922 700, EP 1 183 255 and WO 03074523.

Example 1 below describes the preparation of the agent D in accordance with the following reaction scheme:

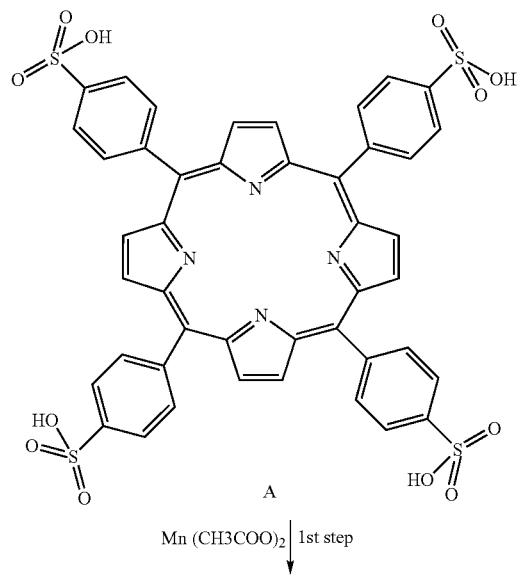

-continued

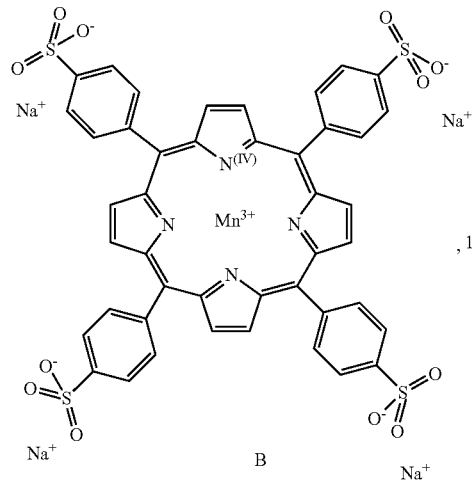

B
Molecular Weight = 983.90
Molecular Formula = C44H24MnN4O12S4

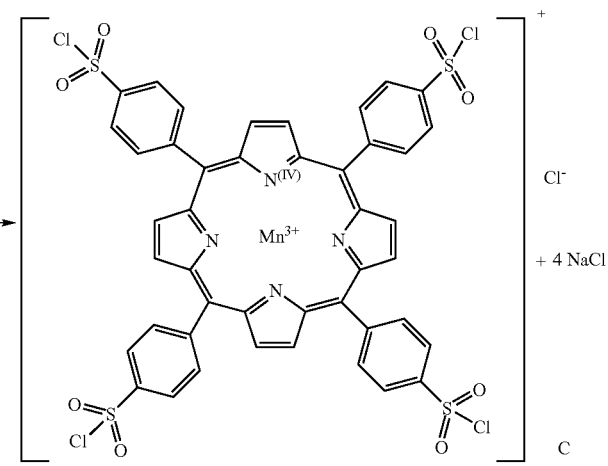

C
Molecular Weight = 1061.71
Molecular Formula = C44H24Cl4MnN4O8S4

3rd Step

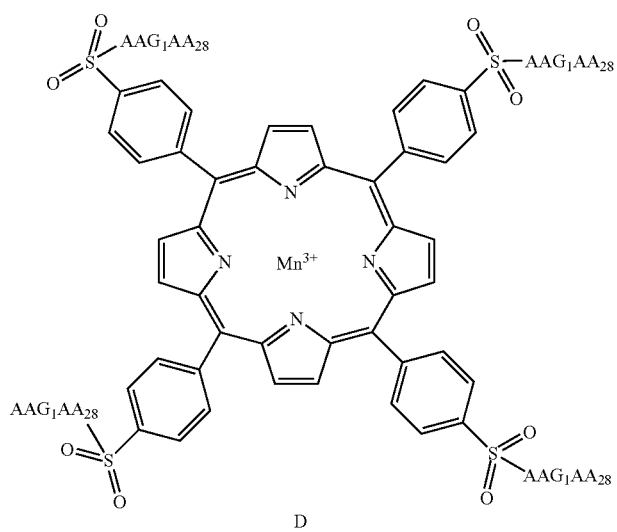

D
$C_{180}H_{252}Br_{12}N_{20}O_{100}S_4Mn$
$M = 5434 \text{ g.mol}^{-1}$ in which $AAG_1AA_{28}$ =

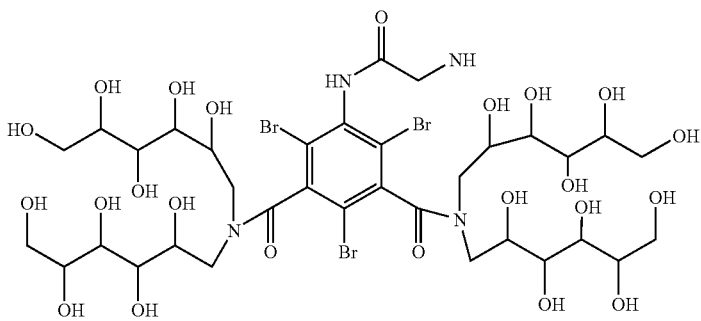

Step 1: Complexing and Oxidation 1 g of compound A is dissolved in 100 ml of CH$_3$COOH in the presence of 4 g of manganese acetate. The resulting solution is stirred, warmed to 115° C. and placed under continuous air suction. The reaction is monitored using a UV spectrometer: the product B which is formed has a specific wavelength at 466 nm (the starting material A has a wavelength at 433 nm). The reaction has come to an end after 4 days at 115° C. The reaction medium is cooled down and then filtered through a fritted glass and washed with hot acetic acid. The precipitate of B which is obtained is taken up in water and this solution is then evaporated in order to remove the acetic acid. The residue which is obtained is dissolved in 250 ml of water. The solution is purified on 10 ml of Chelex. Ion adsorption chromatography is used to check that no more free $Mn^{2+}$ remains.

After evaporation, 560 mg of black crystals of B are obtained.

Mass spectrum (electrospray in negative mode): $(M-2H)^{2-}=492.7$

Retention time: 18.25

Step 2: Chlorination 1 g of compound B obtained in step 1 above is suspended in 5 ml of $SOCl_2$ in the presence of 10 drops of DMF. The reaction medium is stirred and heated at 55° C. for 5 hours. After cooling, the medium is poured into 50 ml of isopropyl ether after which the mixture is filtered and the precipitate is washed and dried in vacuo at room temperature. 1 g of black crystals of C is obtained.

Assay using propylamine: % $Cl_{found}$=% $Cl_{theory}$=24%

Mass spectrum (in positive electrospray): involving prior treatment with propylamine $(M+H)^{+}=1152$ Step 3: Amidation 6.6 g of brominated $AAG_1AA_{28}$ of the formula

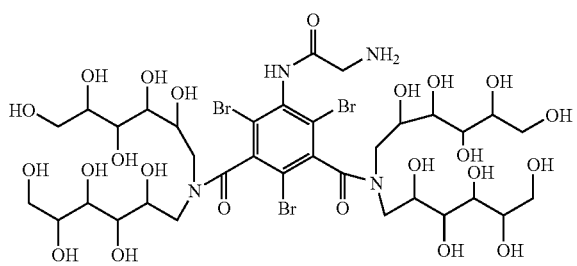

are dissolved in 25 ml of N-methylpyrrolidone in the presence of 0.75 ml of $NEt_3$.

The resulting precipitate is filtered. After 3 Å molecular sieve has been added, 1.5 g of compound C are added in portions. The reaction mixture is stirred and heated at 55° C. for 3 H and is then stirred at room temperature for 12 H. The reaction mixture is poured into 350 ml of EtOH. The resulting precipitate is filtered and then washed and dried. The black crystals of D are dissolved in the minimum amount of water for being chromatographed through a mixture of 50% silanized silica (Merck, 0.063-0.200 mm) and 50% of RP 18 Lichroprep (15-25 µm). The pure product is detached using 0.01 M ammonium acetate. The salts are then removed by filtering through silanized $SiO_2$ (Merck, 0.063-0.200 µm).

Mass spectrum (electrospray in negative mode): $(M-4H)^{4-}=1356.5$. The retention time is 27.88 min.

The description has demonstrated the advantage of porphyrin compounds having high relaxivity at high field. However, it is not limited to these compounds, but also relates to the porphyrin compounds which have a relaxivity at high field which is sufficiently high, typically at least 10 $mmol^{-1}s^{-1}$, for diagnostic use.

The invention also relates to the use, at high field, of porphyrin compounds which are described in the application and which:

are coupled to biological vectors, such as peptides and vitamins, which are able to specifically target a diseased region, are coupled to lipid nanoparticles which may possibly be carried by targeting biovectors.

The invention claimed is:

1. A magnetic resonance imaging method, said method comprising:

administering diagnostically effective dose of a porphyrin compound of the following general formula (I) to a patient:

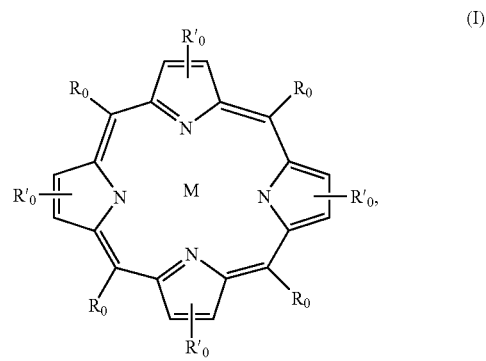

wherein $R'_0$ denotes H, a linear or branched C1-C4 alkyl group or is absent; and $R_0$ denotes:

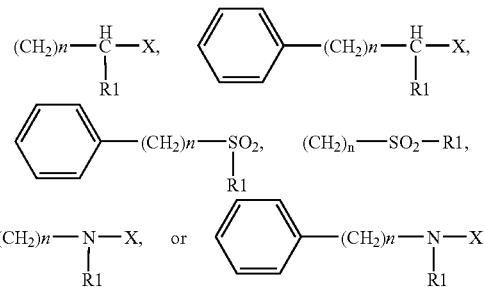

wherein n is an integer between 0 and 8;

each X is identical or different and denotes a hydrogen atom or a $COR_a$, $SO_3R_e$, $CO_2R_a$, $CONR_bR_c$ or $P(R_d)OOH$ group, wherein $R_a$, $R_b$, $R_c$ and $R_e$ are identical or different and respectively denote a hydrogen atom or an optionally hydroxylated ($C_1$-$C_8$) alkyl group, wherein P denotes the phosphorus atom, and $R_d$ denotes an OH group or a ($C_1$-$C_8$)alkyl or ($C_1$-$C_8$)alkoxy group;

each R1 is identical or different and denotes a hydrogen atom or a hydrophilic group which comprises at least three oxygen atoms, whose molecular weight is greater than 200 g/mol, and is selected from the group consisting of:

a polyoxy($C_2$-$C_3$)alkylene group or its $C_1$ to $C_3$ monoethers or monoesters;

a polyhydroxyalkyl, a polyol, and a group of the formula $(R_2G)_e[(R_2G)_iR_3]_h$, wherein:

h=1 or 2;

i=0, 1 or 2;

e=1 to 5;
each $R_2$ is identical or different from each other, and each $R_2$ is absent or denotes a $C_1$ to $C_{14}$ alkylene group, $C_1$ to $C_{14}$ alkoxyalkylene, $C_1$ to $C_{14}$ polyalkoxyalkylene, a phenylene or a saturated or unsaturated heterocyclic group which are optionally substituted by OH, Cl, Br, I or a $(C_1$-$C_8)$alkyl, $(C_1$-$C_8)$alkoxy, $NO_2$, $NR_XR_Y$, $NR_XCOR_Y$, $CONR_XR_Y$ or $COOR_X$ group wherein $R_X$ and $R_Y$ denote, independently of each other, H or a $(C_1$-$C_8)$alkyl group, with the alkyl, alkylene and alkoxy groups being linear, branched or cyclic and being able to be hydroxylated;
each G is identical or different from each other, and each G is absent or denotes an oxygen atom or a CO, OCO, COO, $SO_3$, $OSO_2$, CONR', NR'CO, NR'COO, OCONR', NR', NR'CS, CSNR', $SO_2NR'$, NR'$SO_2$, NR'CSO, OCSNR', NR'CSNR', P(O)(OH)NR' or NR'P(O)—(OH) group wherein R' denotes H, a $(C_1$-$C_8)$alkyl aroup or $R_3$; and
$R_3$ denotes a $C_1$-$C_{14}$ alkyl group; a phenyl group; a $C_1$-$C_{14}$ alkyl group which is substituted, or interrupted by (a) phenyl group(s); a $C_1$-$C_{14}$ alkyleneoxy group; an amino or amido group unsubstituted or substituted by a $C_1$-$C_{14}$ alkyl group which is optionally substituted, or interrupted, by one of the preceding groups; optionally the phenyl, phenylene and heterocyclic groups are substituted by OH, Cl, Br, I or a $(C_1$-$C_8)$alkyl, $(C_1$-$C_8)$alkoxy, $NO_2$, $NR_XR_Y$, $NR_XCOR_Y$, $CONR_XR_Y$ or $COOR_X$ group wherein $R_X$ and $R_Y$ denote, independently of each other, H or a $(C_1$-$C_8)$alkyl group, with the alkyl, alkylene and alkoxy groups being linear, branched or cyclic and being able to be hydroxylated;
on the condition that X and R1 do not simultaneously denote a hydrogen atom;
or $R_0$ denotes phenyl-R;
wherein R denotes R8 or R9,
wherein R8 denotes a group of the general formula
—(O)$_s$—(CH$_2$)$_k$—X—CH$_2$—Y—C=O)-Z,
wherein
s is 0 or 1;
k is 0, 1, 2 or 3;
X is O, a bond or NR10; R10 is $C_1$-$C_4$ acyl, $C_1$-$C_{10}$ alkylsulfonyl, benzenesulfonyl, $C_1$-$C_4$ alkylphenylenesulfonyl, carboxy-$C_1$-$C_6$ alkyl or carboxy-$C_1$-$C_5$ acyl;
Y is a bond or —CHOH; Z-OH or —NR11R12; R11 and R12 are, independently, H or a saturated or unsaturated, linear or branched chain comprising up to 16 carbon atoms which is optionally substituted by from 1 to 6 hydroxyl groups,
wherein R9 is H, F, Cl, Br, I, a linear or branched $C_1$-$C_4$ alkyl chain or a group of the formula
—(O)$_s$—(CH$_2$)$_k$—X—CH$_2$—Y—C=O)-Z
or R denotes CO-A, $SO_2$-A, OR5, R5, W or NH—W;
wherein
A is OH, OR4, NR5R6 or —(NH)$_x$ {Q-(NH)$_y$}$_w$—W;
R4 is $C_1$-$C_6$ alkyl or benzyl;
R5 and R6 are, independently, H or a linear or branched, saturated or unsaturated $C_1$-$C_{16}$ chain which is optionally substituted by one or more hydroxyl or $C_1$-$C_6$ alkoxy groups, or, when R6 is H, R5 is a $C_6$-$C_{10}$ aryl or a $C_1$-$C_6$ alkyl,
or R5 and R6 form, together with a nitrogen atom, a saturated or unsaturated cycle,
x and y are in each case, independently, 0, 1 or 2;
w is 0 or 1;
Q is $C_1$-$C_{20}$ alkylene;
W is H or V—H
with V is a bond or a cyclic, aliphatic or aromatic, linear or branched, hydrocarbon chain comprising up to 20 C atoms which is optionally substituted or interrupted by —NH—, —O—, —S—, —N—, —CO—O—, —O—CO—, (OCH$_2$CH$_2$—), —NH—CO—, —CO—NH—, —NH—NH—, —C$_6$H$_4$—NH—, —C$_6$H$_4$—O— and —C$_6$H$_4$—;
wherein $R_0$ and $R'_0$ in formula I are such that the compound is soluble in a biological medium of said patient and M denotes a paramagnetic metal ion; and
applying a magnetic field to said patient to attain the magnetic resonance image, said magnetic field is in the order of higher than 1.5 Tesla.

2. The method according to claim 1, wherein M is $Mn^{3+}$ manganese.

3. The method according to claim 1 or claim 2, wherein the magnetic field is between 1.5 and 7 T.

4. The method according to claim 1, wherein the porphyrin compound is of the general formula (IV):

(IV)

wherein M in formula (IV) denotes a paramagnetic metal ion, $R'_0$ is absent and R denotes:

$(CH_2)n$—$\overset{H}{\underset{R1}{C}}$—X   or   $(CH_2)_n$—$SO_2$—R1   or $(CH_2)n$—$\underset{R1}{N}$—X wherein n is an integer between 0 and 8,
each X is identical or different and denotes a hydrogen atom or a $COR_a$, $SO_3R_e$, $CO_2R_a$, $CONR_bR_e$ or $P(R_d)$OOH group wherein $R_a$, $R_b$, $R_c$ and $R_e$ are identical or different and respectively denote a hydrogen atom or an optionally hydroxylated $(C_1$-$C_8)$ alkyl group; wherein P denotes the phosphorus atom, and $R_d$ denotes an OH group or a $(C_1$-$C_8)$alkyl or $(C_1$-$C_8)$alkoxy group;
each R1 is identical or different and denotes a hydrogen atom or a hydrophilic group which comprises at least three oxygen atoms, whose molecular weight is greater than 200 g/mol, and is selected from the group consisting of:

a polyoxy($C_2$-$C_3$)alkylene group or its $C_1$ to $C_3$ monoethers or monoesters;
a polyhydroxyalkyl,
a polyol, and
a group of the formula $(R_2G)_e[(R_2G)_iR_3]_h$, wherein:
h=1 or 2;
i=0, 1 or 2;
e=1 to 5;
each $R_2$ is identical or different from each other, and each $R_2$ is absent or denotes a $C_1$ to $C_{14}$ alkylene group; $C_1$ to $C_{14}$ alkoxyalkylene, $C_1$ to $C_{14}$ polyalkoxyalkylene; a phenylene or a saturated or unsaturated heterocyclic group which are optionally substituted by OH, Cl, Br, I or a ($C_1$-$C_8$)alkyl, ($C_1$-$C_8$) alkoxy, $NO_2$, $NR_XR_Y$, $NR_XCOR_Y$, $CONR_XR_Y$ or $COOR_X$ group wherein $R_X$ and $R_Y$ denote, independently of each other, H or a ($C_1$-$C_8$)alkyl group, with the alkyl, alkylene and alkoxy groups being linear, branched or cyclic and being able to be hydroxylated;
each G is identical or different from each other, and each G is absent or denotes an oxygen atom or a CO, OCO, COO, $SO_3$, $OSO_2$, CONR', NR'CO, NR'COO, OCONR', NR', NR'CS, CSNR', $SO_2NR'$, $NR'SO_2$, NR'CSO, OCSNR', NR'CSNR', P(O)(OH)NR' or NR'P(O)—(OH) group wherein R' denotes H, a ($C_1$-$C_8$)alkyl group or $R_3$; and
$R_3$ denotes a $C_1$-$C_{14}$ alkyl group; a phenyl group; a $C_1$-$C_{14}$ alkyl group which is substituted, or interrupted, by (a) phenyl group(s); a $C_1$-$C_{14}$ alkyleneoxy group; an amino or amido group unsubstituted or substituted by a $C_1$-$C_{14}$ alkyl group which is optionally substituted, or interrupted, by one of the preceding groups; optionally the phenyl, phenylene and heterocyclic groups are substituted by OH, Cl, Br, I or a ($C_1$-$C_8$)alkyl, ($C_1$-$C_{C8}$)alkoxy, $NO_2$, $NR_XR_Y$, $NR_XCOR_Y$, $CONR_XR_Y$ or $COOR_X$ group wherein $R_X$ and $R_Y$ denote, independently of each other, H or a ($C_1$-$C_8$)alkyl group, with the alkyl, alkylene and alkoxy groups being linear, branched or cyclic and being able to be hydroxylated;

on condition that X and R1 do not simultaneously denote a hydrogen atom.

5. The method according to claim 1, wherein the porphyrin compound corresponds to the general formula (III):

(III):

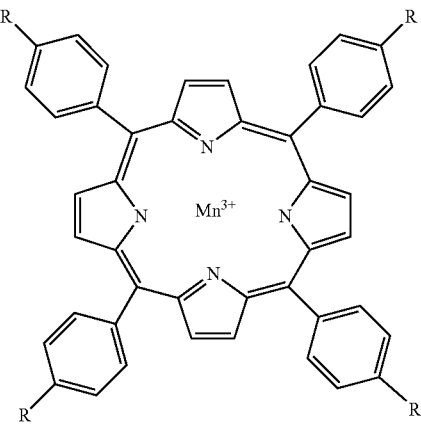

in which R denotes the group $SO_3H$ or $CO_2H$.

6. The method according to claim 5, wherein R denotes the group $CO_2H$.

7. The method according to claim 1, wherein the r1 relaxivity of the porphyrin compound, as measured at a field higher than 1.5 Tesla, is between 10 and 300 $mmol^{-1}s^{-1}$.

8. The method according to claim 1, wherein the porphyrin compound is administered at an administration dose which is between 0.01 and 0.5 mmol/kg.

9. The method of claim 1, wherein the porphyrin compound specifically targets a cancerous tissue of said patient.

10. The method according to claim 4, 7, 8 or 9, wherein the porphyrin compound is depicted by the following formula:

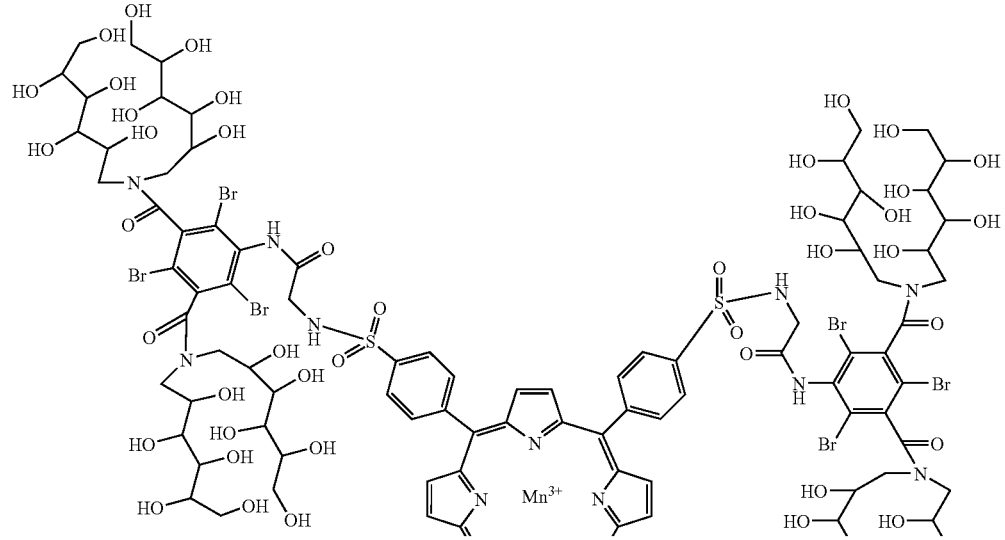

-continued

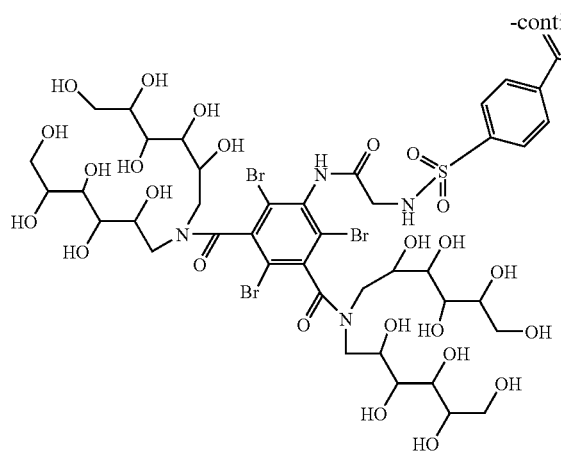
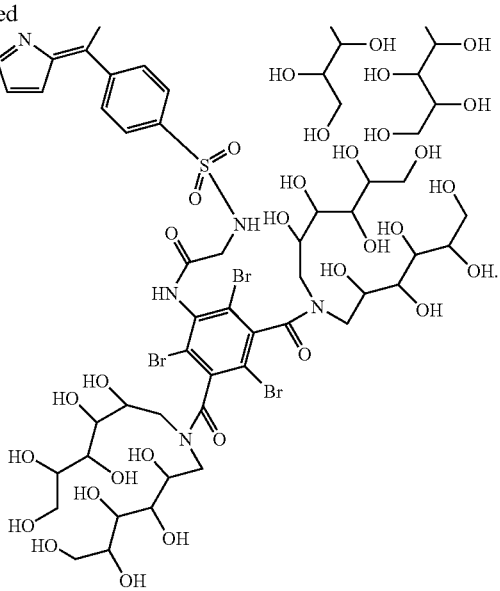

11. A porphyrin compound of the following general formula (IV):

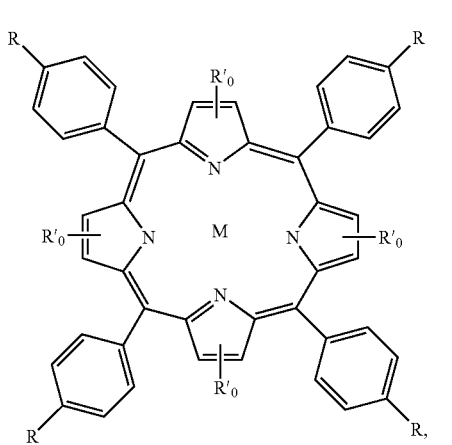

wherein M denotes a paramagnetic metal ion, R'$_0$ is absent and R denotes:

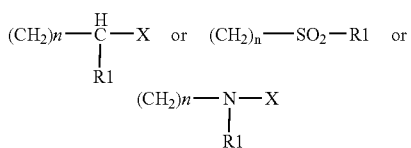

wherein n is an integer between 0 and 8,
each X is identical or different and denotes a COR$_a$, SO$_3$R$_c$, CO$_2$R$_a$, CONR$_b$R$_c$ or P(R$_d$)OOH group in which R$_a$, R$_b$, R$_c$ and R$_e$ are identical or different and respectively denote a hydrogen atom or an optionally hydroxylated (C$_1$-C$_8$) alkyl group; P denotes the phosphorus atom, and R$_d$ denotes an OH group or a (C$_1$-C$_8$)alkyl or (C$_1$-C$_8$)alkoxy group;

each R1, which is identical or different, denotes a hydrophilic group which comprises at least three oxygen atoms, whose molecular weight is greater than 200 g/mol, and is selected from the group consisting of:
a polyoxy(C$_2$-C$_3$)alkylene group or its C$_1$ to C$_3$ monoethers or monoesters,
a polyhydroxyalkyl,
a polyol and
a group of the formula (R$_2$G)$_e$[(R$_2$G)$_i$R$_3$]$_h$, wherein:
h=1 or 2;
i 0, 1 or 2;
e=1 to 5;
each R$_2$ is identical or different from each other, and is absent or denotes a C$_1$ to C$_{14}$ alkylene group; C$_1$ to C$_{14}$ alkoxyalkylene, C$_1$ to C$_{14}$ polyalkoxyalkylene; a phenylene or a saturated or unsaturated heterocyclic group which are optionally substituted by OH, Cl, Br, I or a (C$_1$-C$_8$)alkyl, (C$_1$-C$_8$)alkoxy, NO$_2$, NR$_X$R$_Y$, NR$_X$COR$_Y$, CONR$_X$R$_Y$ or COOR$_X$ group wherein R$_X$ and R$_Y$ denote, independently of each other, H or a (C$_1$-C$_8$)alkyl group, with the alkyl, alkylene and alkoxy groups being linear, branched or cyclic and being able to be hydroxylated;
each G is identical or different from each other, and is absent or denotes an oxygen atom or a CO, OCO, COO, SO$_3$, OSO$_2$, CONR', NR'CO, NR'COO, OCONR', NR', NR'CS, CSNR', SO$_2$NR', NR'SO$_2$, NR'CSO, OCSNR', NR'CSNR', P(O)(OH)NR' or NR'P(O)—(OH) group wherein R' denotes H, a (C$_1$-C$_8$)alkyl group or R$_3$;
R$_3$ denotes a C$_1$-C$_{14}$ alkyl group; a phenyl group; a C$_1$-C$_{14}$ alkyl group which is substituted, or interrupted, by (a) phenyl group(s); a C$_1$-C$_{14}$ alkyleneoxy group; an amino or amido group which is unsubstituted or substituted by a C$_1$-C$_{14}$ alkyl group which is optionally substituted, or interrupted, by one of the preceding groups; optionally the phenyl, phenylene and heterocyclic groups is substituted by OH, Cl, Br, I or a (C$_1$-C$_8$)alkyl, (C$_1$-C$_8$)alkoxy, NO$_2$, NR$_X$R$_Y$, NR$_X$COR$_Y$, CONR$_X$R$_Y$ or COOR$_X$ group wherein R$_X$ and R$_Y$ denote, independently of each other, H or a ($C_1$-$C_8$)alkyl group, with the alkyl, alkylene and alkoxy groups being linear, branched or cyclic and being able to be hydroxylated.

12. A compound as claimed in claim 11, wherein M denotes $Mn^{3+}$.

13. A diagnostic composition comprising:
a compound as claimed in either of claims 11 and 12, and
a pharmaceutically acceptable excipient.

14. The method according to claim 1 or claim 2, wherein the magnetic field is between 2 and 4 T.

15. The method according to claim 4, wherein M in formula (IV) is the paramagnetic metal ion of $Mn^{3+}$.

16. The method according to claim 4, wherein R1 in formula (IV) represents a hydrophile group which comprises at least three oxygen atoms whose molecular weight is greater than 700 g/mol.

17. The porphyrin compound according to claim 11, wherein each R1 which is identical or different denotes a hydrophilic group which comprises at least three oxygen atoms, whose molecular weight is greater than 700 g/mol.

* * * * *